(12) United States Patent
Hirata et al.

(10) Patent No.: US 6,620,977 B1
(45) Date of Patent: Sep. 16, 2003

(54) PROCESS FOR PRODUCING BUTANETRIOL DERIVATIVE

(75) Inventors: Makoto Hirata, Amagasaki (JP); Masafumi Mikami, Amagasaki (JP); Yoshiro Furukawa, Amagasaki (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 09/581,086

(22) PCT Filed: Jan. 28, 1999

(86) PCT No.: PCT/JP99/00355
§ 371 (c)(1),
(2), (4) Date: Jun. 9, 2000

(87) PCT Pub. No.: WO99/38828
PCT Pub. Date: Aug. 5, 1999

(30) Foreign Application Priority Data

Jan. 30, 1998 (JP) .......................................... 10-018802

(51) Int. Cl.⁷ .............................................. C07C 41/18
(52) U.S. Cl. ...................... 568/648; 568/660; 568/679; 568/680
(58) Field of Search ................................ 568/660, 648, 568/679, 680; 558/59; 556/445, 449, 466

(56) References Cited

U.S. PATENT DOCUMENTS

| 5,541,347 A | | 7/1996 | Faul et al. ................... 552/105 |
| 5,665,877 A | * | 9/1997 | Faul et al. ................... 540/469 |
| 5,710,145 A | | 1/1998 | Engel et al. ................. 514/183 |
| 6,015,807 A | * | 1/2000 | Engel et al. ................. 514/183 |

FOREIGN PATENT DOCUMENTS

| EP | 657411 | 6/1995 |
| JP | 04-149151 | 5/1992 |
| JP | 07-215977 | 8/1995 |
| JP | 08-512030 | 12/1996 |
| JP | 09-047296 | 2/1997 |

OTHER PUBLICATIONS

Faul et al., Macrocyclic Bisindolylmaleimides:Synthesis by Inter– and Intramolecular Alkylation, J. Org. Chem., Mar. 1998, American Chemical Society, vol. 63, No. 6, pp. 1961–1973.*

* cited by examiner

Primary Examiner—Rosalynd Keys
(74) Attorney, Agent, or Firm—Jacobson Holman PLLC

(57) ABSTRACT

A process for preparing a butanetriol derivative of the formula (1) useful as intermediates of medicines

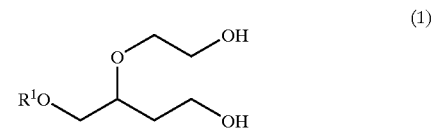

(1)

wherein $R^1$ is the same defined below, which comprises reacting a compound of the formula (3)

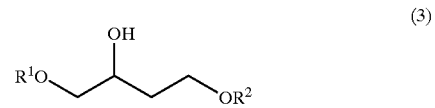

(3)

wherein $R^1$ and $R^2$ are the different protecting groups, and an ethylene glycol derivative in a basic condition to prepare a compound of the formula (4) or (4a)

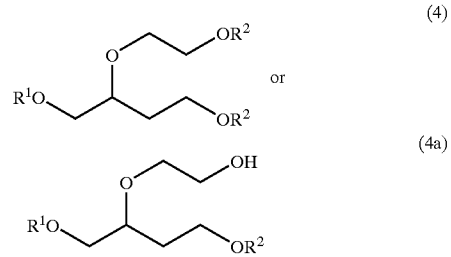

(4)

or (4a)

wherein $R^1$ and $R^2$ are the same defined above, and then subjecting the compound (4) or (4a) to selective deprotection reaction.

22 Claims, No Drawings

PROCESS FOR PRODUCING BUTANETRIOL DERIVATIVE

TECHNICAL FIELD

The present invention relates to a process for preparing a butanetriol derivative, which is important as an intermediate in making antidiabetics having protein kinase C inhibiting activity and relates to a novel intermediate of the butanetriol derivative.

BACKGROUND ART

Butanetriol derivatives are used as intermediates in making antidiabetics having protein kinase C inhibiting activity. It is known that butanetriol derivatives are prepared by reacting glycidyl trityl ether and vinylmagnesium bromide, by allyl-etherification and by ozonolysis of resulting olefin, followed by treatment of resulting aldehyde with sodium borohydride (U.S. Pat. No. 5,541,347).

Glycidyl trityl ether, however is expensive and the reactions with vinylmagnesium bromide and by ozonolysis have to be carried out at lower temperature, −20° C. and −35 to −50° C., respectively. The procedures, therefore are troublesome. Furthermore, ozone is harmful to human body and there is a possibility of explosion. Thus, the known methods are not satisfactory for application to industrially scaled production. The superior method has been desired.

DISCLOSURE OF INVENTION

As a result of extensive investigation on an improved method for preparing butanetriol derivatives, the present inventors have found that butanetriol derivatives can be favorably prepared in industrial scale by using the starting material which is easily available.

The present invention relates to a novel process for preparing a butanetriol derivative, which is important as an intermediate in making antidiabetics having protein kinase C inhibiting activity and relates to a novel intermediate thereof.

The process for preparing a butanetriol derivative (1) of the present invention is shown as the following reaction scheme.

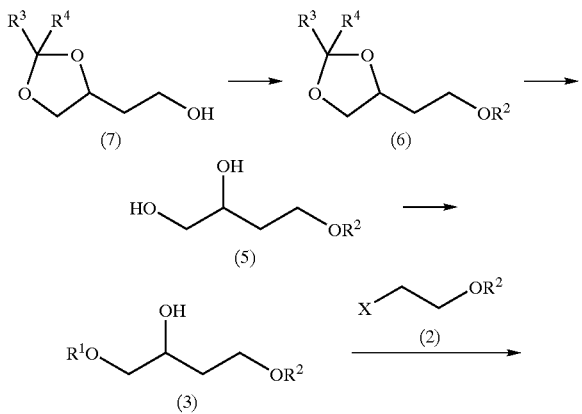

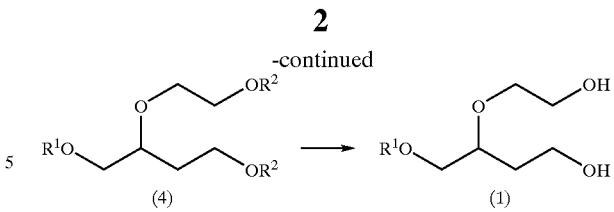

In the above formulae, $R^1$ and $R^2$ are, different from each other, protecting groups for alcohol and said protecting groups are such that only $R^2$ is removed when deprotection reaction is carried out. $R^3$ and $R^4$ are, the same or different, hydrogen, $C_1$–$C_4$ alkyl or phenyl, or may form a $C_3$–$C_6$ cycloalkyl group together with the adjacent carbon atom. X is halogen atom or sulfonyloxy group.

Each step is explained below in detail.

Process for Preparing Compound (6)

Compound (6) is prepared from compound (7).

Introduction of the protecting group ($R^2$) except tetrahydropyranyl group is carried out by etherifying hydroxy group for compound (7) in the presence of a base to give compound (6).

Examples of the protecting group are silyl ether-protecting groups, such as triethylsilyl, tert-butyldimethylsilyl or tert-butyldiphenylsilyl, benzyl-protecting groups, such as benzyl, p-methoxybenzyl or trityl, and acetal-protecting groups such as methoxymethyl etc.

Introduction of tetrahydropyranyl group is carried out by reacting compound (7) and dihydropyrane in the presence of acid catalyst, such as p-toluenesulfonic acid or pyridinium p-toluenesulfonate.

Preferable protecting groups are tert-butyldimethyl-silyl, tert-butyldiphenylsilyl, benzyl and p-methoxybenzyl, especially tert-butyldimethylsilyl and benzyl.

Introduction of the protecting group except tetrahydropyranyl group is carried out by reacting hydroxy group of compound (7) with an alkylating agent in the presence of a base.

Examples of the base used in this reaction are alkali metal or alkaline earth metal hydroxides, such as sodium hydroxide or potassium hydroxide, alkali metal or alkaline earth metal hydrogen carbonates, such as sodium hydrogen carbonate or potassium hydrogen carbonate, alkali metal or alkaline earth metal carbonates, such as sodium carbonate or potassium carbonate, alkali metal or alkaline earth metal hydrides, such as sodium hydride or potassium hydride, organic alkali metal salts, such as dimethyl sodium, n-butyllithium, sec-butyllithium or tert-butyllithium, and alkali metal amides, such as lithium diisopropylamide, potassium diisopropylamide, sodium hexamethyldisilazide, potassium hexamethyldisilazide or lithium hexamethyldisilazide.

Amount of the base is equimole or more than equimole to the substrate, preferably 1.0 to 1.2 moles. Regarding of silyl ether-protecting groups or benzyl-protecting groups, examples of the reacting agent used for protection are silyl halides, such as tert-butyldimethylsilyl chloride, tert-butyldiphenylsilyl chloride, alkyl halides, such as benzyl chloride or benzyl bromide and sulfonic acid esters such as trifluoromethane-sulfonic acid tert-butyldimethylsilyl ester. Regarding acetal-protecting groups, examples of the reacting agent used for protection are alkoxymethyl halides such as methoxymethyl chloride.

Amount of the reacting agent is equimole or more than equimole to the substrate, preferably 1.0 to 1.2 moles.

Examples of a solvent used are aprotic solvents, such as N,N-dimethylformamide, dimethyl sulfoxide or hexamethylphosphoramide, hydrocarbons, such as benzene or toluene, ethers, such as tetrahydrofuran, 1,4-dioxane, glyme, diglyme or triglyme, or a mixture thereof, when as the base are used alkali metal or alkaline earth metal hydrides, such as sodium hydride or potassium hydride, organic alkali metal salts, such as dimethyl sodium, dimethyl potassium, n-butyllithium, sec-butyllithium or tert-butyllithium, or alkali metal amides, such as lithium diisopropylamide, potassium diisopropylamide, sodium hexamethyldisilazide, potassium hexamethyldisilazide or lithium hexamethyldisilazide.

Examples of a solvent used are aprotic solvents, such as N,N-dimethylformamide, dimethyl sulfoxide or hexamethyl-phosphoramide, hydrocarbons, such as benzene or toluene, ethers, such as tetrahydrofuran, 1,4-dioxane, glyme, diglyme or triglyme, halogen compounds, such as dichloromethane, chloroform or 1,2-dichloroethane, water or a mixture with an organic solvent thereof and water, preferably ethers, aprotic solvents or a mixture of an aprotic solvent and water, especially preferably N,N-dimethylformamide, dimethyl sulfoxide or a mixture of dimethyl sulfoxide and water, when as the base are used alkali metal or alkaline earth metal hydroxides, such as sodium hydroxide or potassium hydroxide, alkali metal or alkaline earth metal hydrogen carbonates, such as sodium hydrogen carbonate or potassium hydrogen carbonate, alkali metal or alkaline earth metal carbonates, such as sodium carbonate or potassium carbonate.

The reaction temperature is from $-78°$ C. to reflux temperature of the solvent.

The reaction proceeds without catalyst, but the reaction is promoted in the presence of iodo compounds, such as cesium iodide, potassium iodide or sodium iodide, bromo compounds, such as cesium bromide, potassium bromide or sodium bromide, quaternaryammonium phase transfer catalysts, such as tetrabutylammonium chloride or trimethylbenzyl-ammonium bromide, Crown ethers such as 18-Crown-6, 4-N,N-dimethylaminopyridine, 2,6-lutidine or 4-methoxypyridine, especially effective when a leaving group for the reacting agent used for protection is chlorine atom.

As the reaction promoter, alkali metal bromides or iodides are preferable, especially sodium bromide, potassium bromide, sodium iodide and potassium iodide.

Amount of the reaction promoter is 0.5 to 1.1 moles to compound (7). To use too small amount causes decrease of reaction rate and is not practical.

When $R^2$ is silyl ether-protecting groups, such as triethylsilyl, tert-butyldimethylsilyl or tert-butyldiphenylsilyl, phenyl-substituted methyl-protecting groups, such as benzyl or trityl, or acetal-protecting groups such as methoxymethyl, the protection reaction can be also carried out with halogeno silane compounds, such as trityl chloride or tert-butyldimethylsilyl chloride, alkyl halides, such as benzyl chloride, or benzyl bromide, sulfonic acid esters, such as tert-butyldimethylsilyl trifluoromethanesulfonate, or alkoxymethyl halides such as methoxymethyl chloride in the presence of a tertiary amine, such as triethylamine or pyridine.

Amount of said reagent is equimole or more than equimole to the substrate, preferably 1.0 to 1.2 moles.

Examples of a solvent used are aprotic solvents, such as N,N-dimethylformamide, dimethyl sulfoxide or hexamethyl-phosphoramide, ethers, such as tetrahydrofuran, 1,4-dioxane, glyme, diglyme or triglyme, hydrocarbons, such as benzene or toluene, nitrites such as acetonitrile, halogen compounds, such as dichloromethane, chloroform or 1,2-dichloroethane, or a mixture thereof, preferably aprotic solvents or ethers, especially preferably N,N-dimethylformamide or dimethyl sulfoxide. The reaction is promoted by adding a pyridine derivative, such as 4-N,N-dimethylaminopyridine, 2,6-lutidine or 4-methoxypyridine, preferably 4-N,N-dimethylaminopyridine.

The reaction temperature is from 0C to reflux temperature of the solvent, preferably from room temperature to around 50° C.

On the other hand, introduction of tetrahydropyranyl group is carried out by reacting compound (7) and dihydropyrane in the presence of acid catalyst, such as p-toluenesulfonic acid or pyridinium p-toluenesulfonate.

Amount of dihydropyrane is 1 to 1.2 moles to the substrate.

Examples of a solvent are aprotic solvents, such as N,N-dimethylformamide, dimethyl sulfoxide or hexamethyl-phosphoramide, hydrocarbons, such as benzene or toluene, ethers, such as tetrahydrofuran, 1,4-dioxane, glyme, diglyme or triglyme, halogen compounds, such as dichloromethane, chloroform or 1,2-dichloroethane, or a mixture thereof, preferably aprotic solvents or ethers, especially preferably N,N-dimethylformamide or tetrahydrofuran.

The reaction temperature is from $-78°$ C. to reflux temperature of the solvent.

Process for Preparing Compound (5)

Diol compound (5) is prepared by reacting compound (6) with an acid.

Examples of the acid are mineral acids, such as hydrochloric acid or sulfuric acid, organic acid, such as p-toluenesulfonic acid, benzenesulfonic acid, methanesulfonic acid or trifluoroacetic acid, or Lewis acid, such as boron trifluoride etherate, aluminum trichloride, tin tetrachloride or titanium tetrachloride.

Amount of the acid is equimole or more than equimole to the substrate, preferably 1.0 to 1.2 moles.

The solvents, when the acid is a mineral acid or an organic acid, are alcohols, such as methanol, ethanol or 2-propanol, hydrocarbons, such as benzene or toluene, ethers, such as tetrahydrofuran, 1,4-dioxane, glyme, diglyme or triglyme, or a mixture thereof, preferably alcohols, especially methanol. When Lewis acid is used, examples of the solvent are aprotic solvents, such as N,N-dimethylformamide, dimethyl sulfoxide or hexamethyl-phosphoramide, hydrocarbons, such as benzene or toluene, ethers, such as tetrahydrofuran, 1,4-dioxane, glyme, diglyme or triglyme, or a mixture thereof, preferably aprotic solvents or ethers, especially N,N-dimethylformamide or tetrahydrofuran.

The reaction temperature is from 0° C. to reflux temperature of the solvent, preferably from room temperature to around 50° C.

Process for Preparing Compound (3)

Compound (3) is prepared by protecting a primary hydroxy group for compound (5) with the protecting group ($R^1$) different from the protecting group ($R^2$) $R^1$ is not limited as long as $R^1$ and $R^2$ can be removed under different condition, and $R^1$ is not removed when $R^2$ is deprotected.

The protecting groups ($R^1$) are different from $R^2$ and are silyl ether-protecting groups, such as triethylsilyl, tert-butyldimethylsilyl or tert-butyldiphenylsilyl, phenyl-substituted methyl-protecting groups, such as benzyl, p-methoxybenzyl or trityl, or acetal-protecting groups, such as tetrahydropyranyl or methoxymethyl.

Each of the protecting groups $R^1$ and $R^2$ is selected from silyl ether-protecting groups, phenyl-substituted methyl-protecting groups and acetal-protecting groups. $R^1$ and $R^2$ are different from each other and are such that only $R^2$ is removed, when the deprotection reaction is carried out.

For example, the following combinations are illustrated; $R^1$ is a silyl ether-protecting group and $R^2$ is a phenyl-substituted methyl-protecting group; $R^1$ is a phenyl-substituted methyl-protecting group and $R^2$ is a silyl ether-protecting group; $R^1$ is a silyl ether-protecting group and $R^2$ is an acetal-protecting group; $R^1$ is an acetal-protecting group and $R^2$ is a silyl ether-protecting group; $R^1$ is a phenyl-substituted methyl-protecting group and $R^2$ is an acetal-protecting group.

More concretely, when $R^2$ is a phenyl-substituted methyl-protecting group, such as benzyl or p-methoxybenzyl, $R^1$ is tetrahydropyranyl, methoxymethyl, trityl, or a silyl ether-protecting group, such as tert-butyldimethylsilyl or tert-butyldiphenylsilyl. When $R^2$ is tert-butyldimethylsilyl, $R^1$ is a phenyl-substituted methyl-protecting group, such as benzyl, p-methoxybenzyl or trityl, an acetal-protecting group, such as tetrahydropyranyl or methoxymethyl, or tert-butyldiphenylsilyl more bulky than tert-butyldimethylsilyl.

When $R^2$ is tert-butyldiphenylsilyl, $R^1$ is a phenyl-substituted methyl-protecting group, such as benzyl, p-methoxybenzyl or trityl, an acetal-protecting group such as, tetrahydropyranyl or methoxymethyl, or dimethylthexylsilyl.

When $R^2$ is an acetal-protecting group, such as tetrahydropyranyl or methoxymethyl, $R^1$ is phenyl-substituted methyl-protecting group, such as benzyl, p-methoxybenzyl except trityl, or a silyl ether-protecting group, such as tert-butyldimethylsilyl or tert-butyldiphenylsilyl. The preferable combination of $R^1$ and $R^2$ is that $R^2$ is tert-butyldimethylsilyl, tert-butyldiphenylsilyl, benzyl or p-methoxybenzyl, and $R^1$ is dimethylthexylsilyl or trityl. The especially preferable combination is one that $R^2$ is benzyl and $R^1$ is trityl.

Introduction of these protecting groups is carried out in accordance with the method of introduction of $R^2$ for compound (7) mentioned above.

Process for Preparing Compound (4)

Compound (4) is prepared by reacting compound (3) with ethylene glycol derivative (2) after treating compound (3) with a base.

Examples of leaving group (X) of ethylene glycol derivative (2) are halogen, such as chlorine or bromine, sulfonic acid ester, such as methanesulfonyloxy or p-toluenesulfonyloxy, and examples of $R^2$ of ethylene glycol derivative (2) are the same protecting groups as the protective groups ($R^2$) of compound (3) mentioned above, such as benzyl, tert-butyldimethylsilyl, tert-butyldiphenylsilyl, tetrahydropyranyl or methoxymethyl.

Examples of the base used in this reaction are alkali metal or alkaline earth metal hydroxides, such as sodium hydroxide or potassium hydroxide, alkali metal or alkaline earth metal hydrogen carbonates, such as sodium hydrogen carbonate or potassium hydrogen carbonate, alkali metal or alkaline earth metal carbonates, such as sodium carbonate or potassium carbonate, alkali metal or alkaline earth metal hydrides, such as sodium hydride or potassium hydride, organic alkali metal salts, such as dimethyl sodium, n-butyllithium, sec-butyllithium or tert-butyllithium, or alkali metal amides, such as lithium diisopropylamide, potassium diisopropylamide, sodium hexamethyldisilazide, potassium hexamethyldisilazide or lithium hexamethyldisilazide, preferably alkali metal hydride, alkali metal hydroxide, alkali metal carbonate, especially sodium hydride, sodium hydroxide or potassium hydroxide.

Amount of the base is 1.0–10 moles to the substrate, preferably 1.0 to 2.0 moles.

Examples of a solvent are aprotic solvents such as N,N-dimethylformamide, dimethyl sulfoxide or hexamethylphosphoramide, hydrocarbons, such as benzene or toluene, ethers, such as tetrahydrofuran, 1,4-dioxane, glyme, diglyme or triglyme, or a mixture thereof, when as the base are used alkali metal or alkaline earth metal hydrides, such as sodium hydride or potassium hydride, organic alkali metal salts, such as dimethyl sodium, dimethyl potassium, n-butyllithium, sec-butyllithium or tert-butyllithium, or alkali metal amides, such as lithium diisopropylamide, potassium diisopropylamide, sodium hexamethyldisilazide, potassium hexamethyldisilazide or lithium hexamethyldisilazide.

Examples of a solvent are aprotic solvents such as N,N-dimethylformamide, dimethyl sulfoxide or hexamethylphosphoramide, hydrocarbons, such as benzene or toluene, ethers, such as tetrahydrofuran, 1,4-dioxane, glyme, diglyme or triglyme, halogen compounds, such as dichloromethane, chloroform or 1,2-dichloroethane, water or a mixture with an organic solvent thereof and water, preferably ethers, aprotic solvents or a mixture of an aprotic solvent and water, especially preferably N,N-dimethylformamide, dimethyl sulfoxide or a mixture of dimethyl sulfoxide and water, when as the base are used alkali metal or alkaline earth metal hydroxides, such as sodium hydroxide or potassium hydroxide, alkali metal or alkaline earth metal hydrogen carbonates, such as sodium hydrogen carbonate or potassium hydrogen carbonate, alkali metal or alkaline earth metal carbonates, such as sodium carbonate or potassium carbonate.

The reaction proceeds without catalyst, but the reaction is promoted in the presence of iodo compounds such as cesium iodide, potassium iodide or sodium iodide, bromo compounds, such as cesium bromide, potassium bromide or sodium bromide, quaternaryammonium phase transfer catalysts, such as tetrabutylammonium chloride or trimethylbenzyl-ammonium bromide, Crown ethers such as 18-Crown-6, or pyridine derivatives, such as 4-N,N-dimethylaminopyridine, 2,6-rutidine or 4-methoxypyridine, especially effective when the leaving group of a reactive substance used for protection is chlorine atom.

As the reaction promoter, alkali metal bromides or iodides are preferable, especially sodium bromide, potassium bromide, sodium iodide or potassium iodide.

Amount of the reaction promoter is 0.05 to 1.1 moles to compound (3). To use too small amount causes decrease of the reaction rate and is not practical.

The reaction temperature is from −100° C. to reflux temperature of the solvent, preferably from 0° C. to reflux temperature of the solvent.

The preferable reaction is to react compound (3) with benzyloxyethyl methanesulfonate as ethylene glycol derivative (2), in N,N-dimethylformamide or dimethyl sulfoxide under sodium hydride at 0° C. to room temperature or to react compound (3) with benzyloxyethyl methanesulfonate in N,N-dimethylformamide under sodium hydroxide or potassium hydroxide.

Process for Preparing Compound (1)

Compound (1) is prepared by selectively removing a protective group ($R^2$) of compound (4) When $R^2$ is a phenyl-substituted methyl-protecting group, such as benzyl or p-methoxybenzyl, it is removed under catalytic hydrogenation. Catalysts used in the hydrogenation are heterogeneous catalysts, such as 5% Pt—C, 5%–10% Pd—C, Palladium black or Raney nickel, or homogeneous catalysts such as Wilkinson's complex.

Amount of the catalyst to a substrate is 1–100% by weight. As hydrogen donor, hydrogen gas, cyclohexene, cyclohexadiene and ammonium formate are illustrated.

Solvents used are alcohols, such as ethanol or 2-propanol, esters, such as methyl acetate or ethyl acetate, ethers, such as tetrahydrofuran, 1,4-dioxane, glyme, diglyme or triglyme, hydrocarbons, such as benzene or toluene, or a mixture thereof, preferably alcohols or esters, especially methanol, ethanol or ethyl acetate.

The reaction is carried out under ambient pressure. The reaction temperature is from 0° C. to reflux temperature, preferably from room temperature to reflux temperature.

p-Methoxybenzyl group can be also removed by reacting 2,3-dichloro-5,6-dicyano-1,4-benzoquinone in a solvent, such as ethers, e.g. tetrahydrofuran, 1,4-dioxane, glyme, diglyme or triglyme, or hydrocarbons, such as benzene or toluene.

Preferable deprotection method is subjecting to catalytic reduction with 5% or 10% Pd—C under hydrogen gas in methanol or ethyl acetate under ambient pressure at room temperature.

When $R^2$ is a silyl ether-protecting group such as tert-butyldimethylsilyl, it is deprotected by reacting fluoro anion, such as hydrogen fluoride or tetrabutylammonium fluoride.

Amount of the fluoro anion is 2.0–10 moles to the substrate. Solvents used are ethers, such as tetrahydrofuran, 1,4-dioxane, glyme, diglyme or triglyme, nitriles such as acetonitrile, hydrocarbons, such as benzene or toluene, or a mixture thereof, preferably ethers or nitriles, especially tetrahydrofuran.

The reaction temperature is from 0° C. to reflux temperature of the solvent, preferably from room temperature to reflux temperature of the solvent.

The protective group can be removed by reacting a mineral acid, such as hydrochloric acid or sulfuric acid, an organic acid, such as p-toluenesulfonic acid, benzenesulfonic acid, methanesulfonic acid or trifluoroacetic acid, or a Lewis acid, such as boron trifluoride etherate, aluminum trichloride, tin tetrachloride or titanium tetrachloride in an ether, such as tetrahydrofuran, 1,4-dioxane, glyme, diglyme or triglyme, a hydrocarbon, such as benzene or toluene, or a mixture thereof.

The reaction temperature is from 0° C. to refluxing temperature of the solvent, preferably 0° C. to room temperature. Preferable deprotection method is carried out by reacting 2 moles or more than 2 moles, preferably 2.0–2.2 moles of tetrabutylammonium fluoride to a substrate in tetrahydrofuran at 0° C. to room temperature.

When $R^2$ is an acetal-protecting group, such as tetrahydropyranyl or methoxymethyl, it is removed by treating with an acid. The acid used are mineral acids, such as hydrochloric acid or sulfuric acid, organic acids such as p-toluenesulfonic acid, benzenesulfonic acid, methanesulfonic acid or trifluoroacetic acid, or Lewis acids, such as boron trifluoride etherate, aluminum trichloride, tin tetrachloride or titanium tetrachloride.

The acid is used 0.1–10 moles to a substrate, preferably 2–4 moles.

Solvents used are alcohols, such as methanol, ethanol or 2-propanol, ethers, such as tetrahydrofuran, 1,4-dioxane, glyme, diglyme or triglyme, nitriles such as acetonitrile, hydrocarbons, such as benzene or toluene, or a mixture thereof, preferably ethers or alcohols, especially methanol or ethanol.

The reaction temperature is from 0° C. to reflux temperature, preferably from 0° C. to room temperature.

Preferable deprotection method is carried out by reacting 2 moles of p-toluenesulfonic acid to a substrate in tetrahydrofuran or methanol at 0° C. to room temperature.

Another Process for Preparing Compound (1)

As shown in the following reaction scheme, after reacting compound (3) with a base, compound (4a) is prepared by reacting compound (2a) or ethylene oxide (2b) therewith, and then, by selectively removing the protecting group ($R^2$) of the compound to give compound (1).

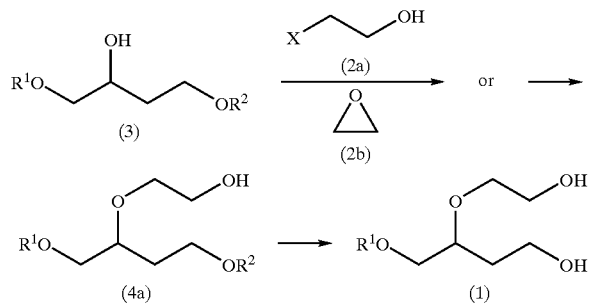

wherein $R^1$, $R^2$ and X are the same as defined above.

Process for Preparing Compound (4a)

Compound (4a) is prepared by reacting compound (2a) or ethylene oxide (2b) with compound (3), after treating compound (3) with a base.

The reaction of compound (3) with compound (2a) or ethylene oxide (2b) is carried out in the almost same manner as the reaction of compound (3) and compound (2) as mentioned above.

By deprotecting $R^2$ for thus obtained compound (4a) there is obtained butanetriol derivative (1).

The deprotection of $R^2$ can be carried out in the same manner as the method for preparing compound (1) by removing the protecting group ($R^2$) of compound (4) as mentioned above.

Another Process for Preparing Compound (3)

Compound (3) is prepared from compound (10) as shown in the following reaction scheme.

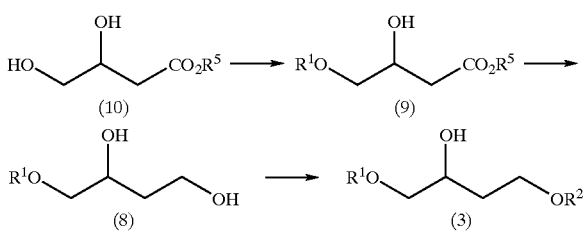

wherein $R^1$ and $R^2$ are the same as defined above, $R^5$ is $C_1$–$C_6$ alkyl, $C_3$–$C_6$ cycloalkyl, phenyl or $C_1$–$C_6$ alkyl substituted phenyl, aralkyl or 2-alkenyl.

Process for Preparing Compound (9)

Compound (9) is prepared by protecting the primary hydroxy group for compound (10) with the protecting group ($R^1$) different from the protecting group ($R^2$) of compound (3), which is prepared in the latter step.

$R^1$ is not limited as long as $R^1$ and $R^2$ can be removed by the different condition, and $R^1$ is not removed when $R^2$ is deprotected. Examples of $R^1$ and the combination of $R^1$ and $R^2$ are the same described in the above section on the process for preparing compound (3).

Introduction of the protecting group is also carried out in the same manner as introduction of $R^2$ to compound (7).

Process for Preparing Compound (8)

Compound (8) is prepared by reducing the ester group of compound (9)

Reducing agents are aluminum-reducing agents, such as lithium aluminum hydride or diisobutyl aluminum hydride, or boron-reducing agents, such as sodium borohydride, lithium borohydride, lithium tri-sec-butyl borohydride, potassium tri-sec-butyl borohydride, boron tetrahydrofuran or boron dimethylsulfide complex, preferably lithium aluminum hydride or sodium borohydride.

The reduction is carried out in a solvent such as ethers, e.g. tetrahydrofuran, 1,4-dioxane, glyme, diglyme or triglyme, or hydrocarbons, e.g. benzene, toluene or a mixture thereof. When sodium borohydride is used, an alcohol, such as methanol, ethanol or propanol may be used as a solvent.

Amount of the reducing agent calculated in hydrido ion is 2.0–15 moles to the substrate.

The reaction temperature is from –100° C. to reflux temperature of the solvent, preferably –78° C. to room temperature.

Another Process for Preparing Compound (3)

Compound (3) is prepared by protecting primary hydroxy group for compound (8) with the protecting group ($R^2$) different from $R^1$.

$R^2$ is not limited as long as $R^1$ and $R^2$ can be deprotected by the different condition and $R^1$ is not removed when $R^2$ is deprotected. Examples of $R^2$ and the combination of $R^1$ and $R^2$ are the same described in the above section on processes for preparing compound (6) and compound (3).

Introduction of the protecting group is also carried out in the same manner as introduction of $R^2$ to compound (7).

Process for Preparing Compound (11)

A compound of the following formula (11) is prepared by bissulfonyl esterification of compound (1) in the presence of a tertiary amine, such as triethylamine or pyridine.

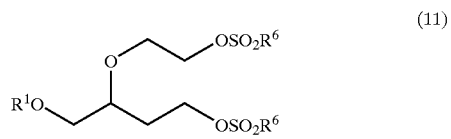

wherein $R^6$ is $C_1$–$C_6$ alkyl, $C_3$–$C_6$ cycloalkyl, substituted or non-substituted $C_1$–$C_6$ alkyl, halogeno phenyl or nitro phenyl, and $R^1$ is the same as defined above.

By bissulfonyl esterification, crystallizabilty of the product becomes good and therefore, it becomes easy to purify the product by recrystallization.

Sulfonyl halides, such as methanesulfonyl chloride, methanesulfonyl bromide, p-toluenesulfonyl chloride, benzenesulfonyl chloride, or sulfonic acid anhydride such as methanesulfonic acid anhydride are used in the sulfonyl esterification.

Amount of the esterification agent is 2 moles or more than 2 moles to the substrate, preferably 2.0 to 2.2 moles.

Examples of a solvent are aprotic solvents, such as N,N-dimethylformamide, dimethyl sulfoxide or hexamethylphosphoramide, ethers, such as tetrahydrofuran, 1,4-dioxane, glyme, diglyme or triglyme, nitriles such as acetonitrile, halogen compounds, such as dichloromethane, chloroform or 1,2-dichloroethane, or a mixture thereof.

The reaction is promoted by addition of about 0.01 mole of 4-N,N-dimethylaminopyridine.

The reaction temperature is from –100° C. to reflux temperature of the solvent, preferably from 0° C. to room temperature.

When compounds (7) and (10) are optically active compounds, optically active compound (1) and optically active intermediates (3)–(6), (4a), (8)–(9) and (11) can be obtained. When natural L-malic acid is used as an optically active starting material, (S) formed compound is obtained. When unnatural D-malic acid is used as an optically active starting material, (R) formed compound is obtained.

These compounds are led to compound (10) by two steps and to compound (7) by 3 steps.

It is also possible to use β-hydroxy-γ-butyrolactone as an optically active starting material. β-Hydroxy-γ-butyrolactone is prepared by the method described in Japanese Patent Publication A 9-47296, and the compound can be led to compound (10) by the method described in Japanese Patent Publication A 4-149151.

Significant racemization does not occur during synthesis of these optically active compounds and therefore, there is obtainable compound (1) with highly optical purity.

Starting compounds (2), (7) and (10) are prepared as follows.

Compound (7) is prepared by acetalization of the adjacent hydroxy groups of 1,2,4-butanetriol in the presence of acid catalyst.

Examples of acetalization agents are ketones, such as acetone, diethyl ketone, benzophenone, cyclohexanone, aldehydes, such as acetoaldehyde or benzaldehyde, dialkoxyacetals of ketone, such as 2,2-dimethoxypropane or 3,3-dimethoxypentane, or enol ethers of ketone such as 2-methoxypropene.

Examples of the acid catalysts are mineral acids, such as hydrochloric acid or sulfuric acid, organic acids, such as p-toluenesulfonic acid, benzenesulfonic acid, methanesulfonic acid or trifluoroacetic acid, or Lewis acids, such as boron trifluoride etherate, aluminum trichloride, tin tetrachloride, or titanium tetrachloride.

Amount of the acid catalyst is 0.05–0.1 mole to the substrate.

Examples of the solvents are aprotic solvents, such as N,N-dimethylformamide, dimethyl sulfoxide or hexamethylphosphoramide, ethers, such as tetrahydrofuran, 1,4-dioxane, glyme, diglyme or triglyme, halogen compounds, such as dichloromethane, chloroform or 1,2-dichloroethane, or acetalization agents themselves, preferably aprotic solvents or acetalization agents themselves, especially preferably N,N-dimethylformamide or acetone.

For example, a compound, wherein $R^3$ and $R^4$ are methyl, is prepared by a method described in the literature (J. Org. Chem., 53, 4495 (1988), that is, by reacting 2,2-dimethoxypropane in the presence of catalytic amount of p-toluenesulfonic acid in N,N-dimethylformamide.

Ethylene glycol derivative (2) is prepared by a method described in the literature (J. Am. Chem. Soc., 60, 1472–1473 (1938). For example, a compound (2), wherein $R^2$ is benzyl, is prepared by reacting 0.25 moles of benzyl bromide or benzyl chloride with 5 moles of ethylene glycol in which 0.25 mole of potassium hydroxide was dissolved. Furthermore, by halogenation of another hydroxy group with thionyl chloride or carbon tetrachloride, or sulfonyl esterification of another hydroxy group with methanesulfonyl chloride or p-toluenesulfonyl chloride, there is obtainable a compound (2), wherein X is a leaving group. A compound, wherein $R^2$ is another protective group, is prepared by using tert-butyldimethylsilyl chloride or methoxymethyl chloride in stead of benzyl halide.

Compound (10) is prepare by reducing malic acid ester, such as methyl ester, ethyl ester, propyl ester, isopropyl ester, butyl ester, cyclohexyl ester, phenyl ester, 4-methylphenyl ester, benzyl ester or allyl ester in a method described in the literature (Chem. Lett., 1984, 1389–1392), namely by selectively reducing one of ester groups with boron dimethylsulfide or sodium borohydride in tetrahydrofuran at room temperature.

On the other hand, compound (10) is prepared by reacting β-hydroxy-γ-butyrolactone with alcohol in acidic condition or by subjecting it to ring opening reaction with alkoxide, such as sodium methoxide or sodium ethoxide.

BEST MODE FOR CARRYING OUT THE INVENTION

The present invention is explained by following examples, but scope of the invention should not be limited by these examples.

EXAMPLE 1

(1) Preparation of (S)-4-(2-Hydroxyethyl)-2,2-dimethyl-1,3-dioxolane (12)

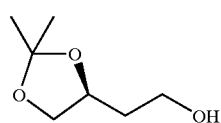

(12)

To a solution of (s)-1,2,4-butanetriol (0.842 g, 7.9 mmol) dissolved in acetone (12 ml) was added p-toluenesulfonic acid hydrate (20 mg) and the mixture was stirred for 21 hours at room temperature. Sodium carbonate (20 mg) was added to the mixture. After stirring for 1 hour, the mixture was filtered and condensed in vacuo to give (S)-4-(2-hydroxyethyl)-2,2-dimethyl-1,3-dioxolane (1.023 g, yield 88%).

(2) Preparation of (S)-4-(2-Benzyloxyethyl)-2,2-dimethyl-1,3-dioxolane (13)

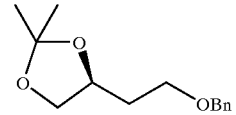

(13)

Sodium hydride (1.33 g, 33.3 mmol, 60% in oil) was loaded under argon circumstance in three-necked flask and hexane (20 ml) was added thereto. After stirring for a while, it was allowed to stand and the supernatant was removed by syringe. By repeating this procedure three times, the oil of sodium hydride was removed. After drying in vacuo, anhydrous N,N-dimethylformamide (DMF) (5 ml) was added and the mixture was cooled at 0° C. (S)-4-(2-Hydroxyethyl)-2,2-dimethyl-1,3-dioxolane (4.42 g, 30.25 mmol) in DMF (8 ml) was dropped to the mixture over a one hour period by taking care of the temperature and then the mixture was stirred for 1 hour. Benzyl chloride (3.83 ml, 33.3 mmol) in DMF (3 ml) was dropped to the solution over a one hour period in the range of 0° C. and 5° C. and then the solution was stirred for 4 hours. After stirring water (20 ml) was added to the solution and the solution was extracted with ethyl acetate. The extract was washed with water (40 ml) twice and with saturated brine once, dried on sodium sulfate, filtered and condensed in vacuo. The residue was subjected to silica gel chromatography to give (S)-4-(2-benzyloxyethyl)-2,2-dimethyl-1,3-dioxolane (6.32 g, yield 88%).

(3) Preparation of (S)-4-Benzyloxy-1,2-butandiol (14)

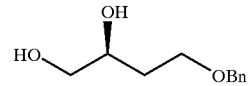

(14)

In methanol (50 ml) were dissolved (S)-4-(2-benzyloxyethyl)-2,2-dimethyl-1,3-dioxolane (2.06 g, 8.73 mmol) and p-toluenesulfonic acid hydrate (1.68 g, 8.8 mmol), and the solution was stirred at room temperature for 24 hours. After removal of methanol in vacuo, aqueous saturated sodium hydrogen carbonate was added to neutralize the solution. The solution was extracted with ethyl acetete and the extract was washed with saturated brine, dried on sodium sulfate, filtered, and condensed in vacuo. The residue was subjected to silica gel chromatography to give (S)-4-benzyloxy-1,2-butanediol (1.70 g, yield 99%).

(4) Preparation of (S)-4-Benzyloxy-1-trityloxy-2-butanol (15)

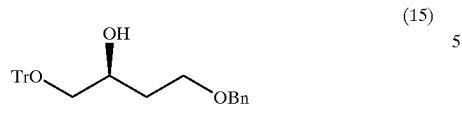

(15)

In toluene (100 ml) were dissolved (S)-4-benzyloxy-1,2-butanediol (25.8 g, 0.132 mol), triethylamine (20.2 ml, 0.145 mol) and 4-N,N-dimethylaminopyridine (DMAP) (0.80 g, 6.58 mmol). After cooling in ice bath, trityl chloride (36.69 g, 0.1316 mol) was added to the solution and the mixture was stirred at room temperature for 10 hours. The mixture was condensed in vacuo, diluted with ethyl acetate, washed with water and then saturated brine, dried on sodium sulfate, filtered and condensed in vacuo to give (S)-4-benzyloxy-1-trityloxy-2-butanol quantitatively (55.89, yield 100%).

$[\alpha]_D^{25}$ 2.29° (C=1.072, CHCl$_3$). $^1$H-NMR (270 MHz, CDCl$_3$) δ: 1.74–1.82 (2H, m), 2.82 (1H, d, J=2.7 Hz), 3.13 (2H, d, J=5.4 Hz), 3.54–3.67 (2H, m), 4.00 (1H, br.s), 4.46 (2H, s), 7.19–7.36 (12H, m), 7.40–7.45 (8H, m). $^{13}$C-NMR (67.8 MHz, CDCl$_3$) δ: 33.90, 67.41, 67.97, 69.91, 73.19, 86.54, 127.00, 127.69, 127.79, 127.89, 128.37, 128.58, 138.09, 143.91.

(5) Preparation of (S)-4-Benzyloxy-2-(2-benzyloxyethoxy)-1-trityloxybutane (16)

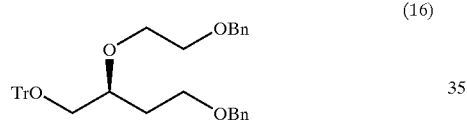

(16)

Sodium hydride (6.32 g, 0.158 mmol, 60% in oil) was loaded under argon circumstance in three-necked flask and hexane (100 ml) was added thereto. After stirring for a while, it was allowed to stand and the supernatant was removed by syringe. By repeating this procedure three times, the oil of sodium hydride was removed. After drying in vacuo anhydrous dimethyl sulfoxide (DMSO) (30 ml) was added and the solution was stirred at 60° C. for 1 hour. After cooling to room temperature, (S)-4-benzyloxy-1-trityloxy-2-butanol (55.89 g, 0.132 mol) in DMSO (40 ml) was gradually dropped at room temperature to the solution and then the solution was stirred for 30 minutes. To the solution was gradually dropped 2-benzyloxyethyl methanesulfonate (33.4 g, 0.145 mol) in DMSO (40 ml) at room temperature and then the solution was stirred for 12 hours. To the reaction mixture was added water (120 ml) and the solution was extracted with ethyl acetate. The extract was washed with water (150 ml) twice and with saturated brine once, dried on sodium sulfate, filtered and condensed in vacuo. The residue was subjected to silica gel chromatography to give (S)-4-benzyloxy-2-(2-benzyloxyethoxy)-1-trityloxybutane (55.0 g, yield 75%).

$[\alpha]_D^{25}$-13.77° (C=1.032, CHCl$_3$). $^1$H-NMR (270 MHz, CDCl$_3$) δ: 1.75–1.87 (2H, m), 3.12–3.16 (2H, m), 3.19–3.68 (6H, m), 3.81–3.89 (1H, m), 4.41 (2H, s), 4.53 (2H, s), 7.19–7.34 (19H, m), 7.44–7.47 (6H, m). $^{13}$C-NMR (67.8 MHz, CDCl$_3$) δ: 32.53, 66.11, 66.75, 69.76, 69.94, 72.87, 73.01, 76.65, 86.51, 126.85, 127.44, 127.62, 127.70, 128.28, 128.36, 128.44, 128.64, 128.71, 138.40, 138.54, 144.10.

(5') Preparation of (S)-4-Benzyloxy-2-(2-benzyloxyethoxy)-1-trityloxybutane (16)

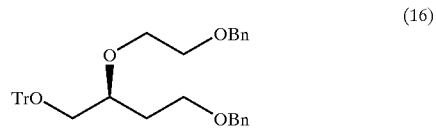

(16)

Sodium hydride (6.32 g, 0.158 mmol, 60% in oil) was loaded under argon circumstance in three-necked flask and hexane (100 ml) was added thereto. After stirring for a while, it was allowed to stand and the supernatant was removed by syringe. By repeating this procedure three times, the oil of sodium hydride was removed. After drying in vacuo anhydrous dimethyl sulfoxide (DMSO) (30 ml) was added and the solution was stirred at 60° C. for 1 hour. After cooling to room temperature, (S)-4-benzyloxy-1-trityloxy-2-butanol (55.89 g, 0.132 mol) in DMSO (40 ml) was gradually dropped at room temperature to the solution and then the solution was stirred for 30 minutes. To the solution was gradually dropped 2-benzyloxyethyl methanesulfonate (33.4 g, 0.145 mol) in DMSO (40 ml) at room temperature and then the solution was stirred for 12 hours. To the reaction mixture was added water (120 ml) and the solution was extracted with ethyl acetate. The extract was washed with water (150 ml) twice and with saturated brine once, dried on sodium sulfate, filtered and condensed in vacuo. The residue was subjected to silica gel chromatography to give (S)-4-benzyloxy-2-(2-benzyloxyethoxy)-1-trityloxybutane (70.8 g, yield 97%).

(6) Preparation of (S)-3-(2-Hydroxyethoxy)-4-trityloxy-butanol (17)

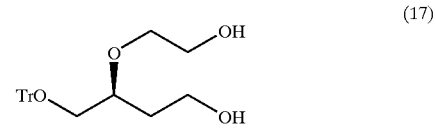

(17)

(S)-4-Benzyloxy-2-(2-benzyloxyethoxy)-1-trityloxybutane (51 mg, 0.092 mmol) was dissolved in ethyl acetate (3 ml). To the solution was added 5% Pd—C (5.0 mg) and the mixture was stirred under an atmosphere of hydrogen for 15 hours at 50° C. After filtering off catalyst, the filtrate was condensed in vacuo, and the residue was subjected to silica gel chromatography to give (S)-3-(2-hydoxyethoxy)-4-trityloxybutanol (28 mg, yield 78%).

EXAMPLE 2

(1) Preparation of (S)-Ethyl 3-Hydroxy-4-trityloxybutanoate (18)

(18)

To (S)-ethyl 3,4-dihydroxybutanoate (1.40 g, 9.45 mmol) in methylene chloride (20 ml) were added triethylamine (1.15 g, 11.36 mmol) and DMAP (17 mg, 0.139 mmol) and the solution was cooled in ice bath. Trityl chloride (2.90 g, 10.4 mol) in methylene chloride (15 ml) was dropped to the solution under stirring and then stirred at room temperature over night. The reaction mixture was washed with saturated ammonium chloride and then saturated brine, dried on magnesium sulfate, filtered and condensed in vacuo. The residue was subjected to silica gel chromatography to give (S)-ethyl 3-hydroxy-4-trityloxybutanoate (1.11 g, yield 31%).

m.p. 98.8–101.1° C. $[\alpha]_D{}^{25}$ −13.1° (C=1.0, EtOAc). $^1$H-NMR (270 MHz, CDCl$_3$) δ: 1.23 (3H, t, J=8.1 Hz), 2.54 (2H, q, J=2.7 Hz), 2.94 (1H, d, J=2.7 Hz), 3.17 (2H, d, J=5.4 Hz), 4.13 (2H, q, J=8.1 Hz), 4.22 (1H, m), 7.21–7.32 (9H, m), 7.40–7.45 (6H, m). $^{13}$C-NMR (67.8 MHz, CDCl$_3$) δ: 14.10, 38.51, 60.63, 66.52, 67.55, 86.68, 127.05, 127.81, 128.59, 143.70, 172.21.

(2) Preparation of (S)-1-Trityloxy-2,4-butandiol (19)

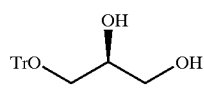
(19)

In ethanol (10 ml) was dissolved (S)-ethyl 3-hydroxy-4-trityloxybutanoate (0.37 g, 0.975 mmol). Sodium borohydride (0.238 g, 6.29 mmol) was added to the solution and the solution was stirred at room temperature over night. Acetic acid was added to neutralize the solution. The solution was diluted with water (100 ml) and extracted with ethyl acetate. The extract was washed with saturated brine, dried on magnesium sulfate, filtered, and condensed in vacuo. The residue was subjected to silica gel chromatography to give (S)-1-trityloxy-2,4-butanediol (0.28 g, yield 82%).

m.p. 68.8–70.9° C. $[\alpha]_D{}^{25}$ 5.20° (C=0.607, CHCl$_3$). $^1$H-NMR (270 MHz, CDCl$_3$) δ: 1.64 (2H, q, J=5.4 Hz), 2.94 (2H, br.s), 3.10 (1H, d, J=2.7 Hz), 3.12 (1H, d, J=2.7 Hz), 3.73 (2H, m), 4.00 (1H, m), 7.21–7.31 (9H, m), 7.38–7.45 (3H, m) $^{13}$C-NMR (67.8 MHz, CDCl$_3$) δ: 34.97. 61.10, 67.56, 70.83, 86.74, 127.13, 127.87, 128.61, 143.72.

(3) Preparation of (S)-4-tert-Butyldimethylsilyloxy-1-trityloxy-2-butanol (20)

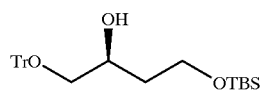
(20)

(S)-1-Trityloxy-2,4-butanediol (1.64 g, 4.7 mmol) and imidazole (0.321 g, 4.715 mmol) were dissolved in DMF (20 ml) and the solution was cooled to 0° C. To the solution was dropped tert-butyldimethylsilyl chloride (0.5 ml, 1.44 mmol, 50% in toluene). After stirring for 1 hour, again to the solution was dropped tert-butyldimethylsilyl chloride (0.5 ml, 1.44 mmol) and the solution was stirred for 1 hour. Further tert-butyldimethylsilyl chloride (0.6 ml, 1.73 mmol) was added to the solution and the solution was stirred over night at room temperature. After dilution with toluene (100 ml), the solution was washed with water (100 ml) twice and saturated brine once, dried on magnesium sulfate, filtered and condensed in vacuo. The residue was subjected to silica gel chromatography to give (S)-4-tert-butyldimethylsilyloxy-1-trityloxy-2-butanol (1.80 g, yield 82.6%).

$[\alpha]_D{}^{25}$ 0.30° (C=1.075, CHCl$_3$). $^1$H-NMR (270 MHz, CDCl$_3$) δ: 0.03 (3H, s), −0.01 (3H, s), 0.85 (9H, s), 1.64–1.73 (2H, m), 3.04–3.15 (2H, m), 3.99 (1H, br.s), 7.17–7.30 (9H, s), 7.39–7.43 (6H, m) $^{13}$C-NMR (67.8 MHz, CDCl$_3$) δ: 5.53, 18.14, 25.86, 35.70, 61.31, 67.41, 70.03, 86.50, 126.98, 127.88, 128.67, 144.00.

(4) Preparation of (S)-4-tert-Butyldimethylsilyloxy-2-(2-tert-butyldimethylsilyloxyethoxy)-1-trityloxybutane (21)

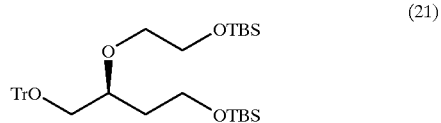
(21)

Sodium hydride (2.11 g, 52.7 mmol, 60% in oil) was loaded under argon circumstance in three-necked flask and hexane (30 ml) was added thereto. After stirring for a while, it was allowed to stand and the supernatant was removed by syringe. By repeating this procedure three times, the oil of sodium hydride was removed. After drying in vacuo anhydrous dimethyl sulfoxide (DMSO) (10 ml) was added and the solution was stirred at 60° C. for 1 hour. After cooling to room temperature, (S)-4-tert-butyldimethylsilyloxy-1-trityloxy-2-butanol (20.36 g, 44.0 mol) in DMSO (12 ml) was gradually dropped at room temperature to the solution and then the solution was stirred for 30 minutes. To the solution was gradually dropped 2-tert-butyldimethylsilyloxyethyl methanesulfonate (12.28 g, 48.3 mol) in DMSO (12 ml) at room temperature and then the solution was stirred for 12 hours. To the reaction mixture was added water (40 ml) and the solution was extracted with ethyl acetate. The extract was washed with water (50 ml) twice and with saturated brine once, dried on sodium sulfate, filtered and condensed in vacuo. The residue was subjected to silica gel chromatography to give (S)-4-tert-butyldimethylsilyloxy-2-(2-tert-butyldimethylsilyloxyethoxy)-1-trityloxybutane (11.2 g, yield 55%).

(5) Preparation of (S)-3-(2-Hydroxyethoxy)-4-trityloxy-butanol (17)

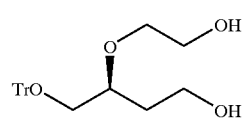
(17)

To (S)-4-tert-butyldimethylsilyloxy-2-(2-tert-butyldimethylsilyloxyethoxy)-1-trityloxybutane (32 mg, 0.053 mmol) in dried tetrahydrofuran (THF) (2 ml) was added tetrabutylammonium fluoride (0.10 ml, 0.11 mmol, 1.1 M in THF) and the mixture was stirred for 1.5 hours at room temperature. A small amount of saturated ammonium chloride was added to the reaction mixture. The solution was dried on sodium sulfate, filtered and condensed in vacuo. The residue was subjected to silica gel chromatography to give (S)-3-(2-hydroxyethoxy)-4-trityloxybutanol (16 mg, yield 75%).

EXAMPLE 3

(1) Preparation of (S)-4-Benzyloxy-1-trityloxy-2-butanol (15)

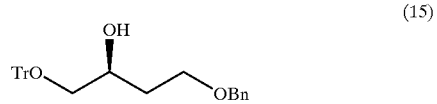
(15)

Sodium hydride (74 mg, 1.85 mmol, 60% in oil) was loaded under argon circumstance in three necked flask and hexane (2 ml) was added thereto. After stirring for a while, it was allowed to stand and the supernatant was removed by syringe. By repeating this procedure three times, the oil of sodium hydride was removed. After drying in vacuo anhydrous dimethyl sulfoxide (DMSO) (2 ml) was added and the solution was cooled to 0° C. (S)-1-Trityloxy-2,4-butandiol (0.62 g, 1.68 mmol) prepared by Example 2-(2) in DMSO (3 ml) was dropped by taking care of the temperature over a one hour period at room temperature to the solution. Then the solution was stirred for 1 hour. To the solution was dropped benzyl chloride (0.213 ml, 1.85 mol) in DMSO (3 ml) over a one hour period at the range of 0° C. to 5° C. and then the solution was stirred for 4 hours. To the reaction mixture was added water (5 ml) and the solution was extracted with ethyl acetate. The extract was washed with water (8 ml) twice and with saturated brine once, dried on sodium sulfate, filtered and condensed in vacuo. The residue was subjected to silica gel chromatography to (S)-4-benzyloxy-1-trityloxy-2-butanol (0.32 g, yield 45%).

(2) Preparation of (S)-3-(2-Hydroxyethoxy)-4-trityloxy-butanol (17)

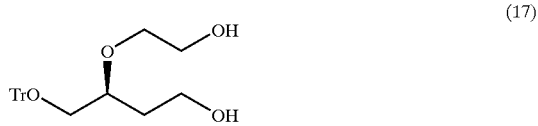
(17)

By using (S)-4-benzyloxy-1-trityloxy-2-butanol(0.25 g, 0.59 mmol), compound (15) prepared by Example 3-(1), and in the same manner of Examples 1-(5) and (6), (S)-3-(2-hydroxyethoxy)-4-trityloxybutanol (0.166 g, 0.42 mmol, yield 72%) was prepared by two steps from compound (15).

EXAMPLE 4

Preparation of (S)-3-[(2-Methylsulfonyloxy) ethoxy]-4-trityloxybutyl Methanesulfonate (22)

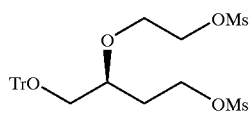
(22)

In toluene (120 ml) were dissolved crude (S)-3-(2-benzyloxyethoxy)-4-trityloxybutanol (29.4 g) without silica gel chromatography prepared in the same method as Example 1, and triethylamine (23 ml, 0.165 mol). To the solution was added portionwise methanesulfonyl chloride (12.2 ml, 0.1575 mol) under ice cooling at the range of 0° C. to 5° C. Then, the solution was stirred at the same temperature for 3 hours. The solution was condensed in vacuo, diluted with ethyl acetate, washed with water and saturated brine, dried on sodium sulfate, filtered and condensed in vacuo to give crude (S)-3-[(2-methylsulfonyloxy) ethoxy]-4-trityloxybutyl methanesulfonate (38.64 g). The crude product was recrystallized twice from a mixture of ethyl acetate and heptane to give purified product (18.15 g, yield 44%).

m.p. 97.2–99.5° C. $[\alpha]_D^{25}$ −15.78 (C=1.0, CHCl$_3$).

What is claimed is:

1. A process for preparing a butanetriol derivative of the formula (1)

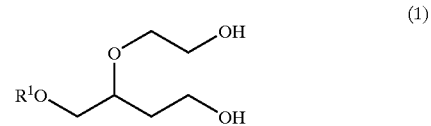
(1)

which comprises subjecting a compound of the following formula (4) or (4a)

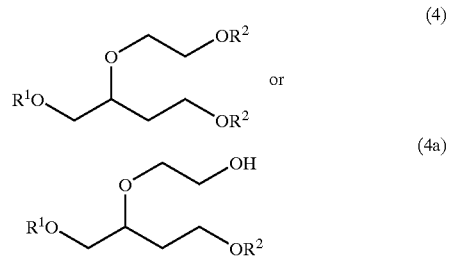
(4)

or (4a)

wherein $R^1$ and $R^2$ are different protecting groups for alcohol to deprotection reaction such that only $R^2$ is removed.

2. A process for preparing a butanetriol derivative of the formula (1)

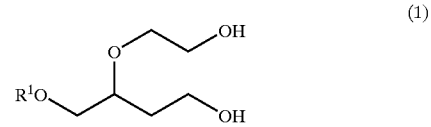
(1)

wherein $R^1$ is the same defined above, which comprises reacting a compound of the formula (3)

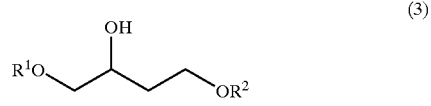
(3)

wherein $R^1$ and $R^2$ are the same defined above, and a compound of the formula (2)

(2)

wherein X is halogen atom or sulfonyloxy group, and $R^2$ is the same as defined above, in a basic condition to prepare a compound of the formula (4)

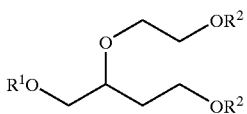
(4)

wherein $R^1$ and $R^2$ are the same defined above, and then subjecting the compound (4) to deprotection reaction.

3. A process for preparing a butanetriol derivative of the formula (1)

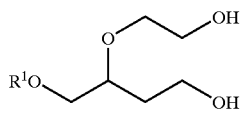
(1)

wherein $R^1$ is the same defined above, which comprises reacting a compound of the formula (3)

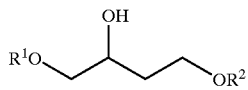
(3)

wherein $R^1$ and $R^2$ are the same defined above, and a compound of the following formula (2a)

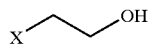
(2a)

wherein X is halogen atom or sulfonyloxy group, or ethylene oxide in a basic condition to prepare a compound of the formula (4a)

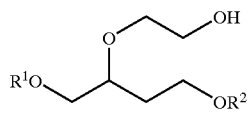
(4a)

wherein $R^1$ and $R^2$ are the same defined above, and then subjecting the compound (4a) to deprotection reaction.

4. A process for preparing a compound (1) which comprises protecting primary hydroxy group for a compound of the formula (5)

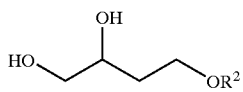
(5)

wherein $R^2$ is the same as defined above, and then carrying out the process of claim 2.

5. A process for preparing a compound (1) which comprises protecting a compound of the formula (7)

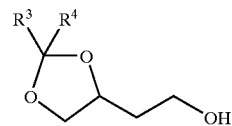
(7)

wherein $R^3$ and $R^4$ are the same or different and are hydrogen, $C_1$–$C_4$ alkyl or phenyl, or may form a $C_3$–$C_6$ cycloalkyl with the adjacent carbon atom, with a protecting agent of alcohol to prepare a compound of the formula (6)

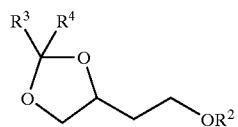
(6)

wherein $R^2$, $R^3$ and $R^4$ are the same as defined above, and then treating the compound (6) with an acid to prepare a compound (5) and then carrying out the process of claim (4).

6. A process for preparing a compound (1) which comprises protecting primary hydroxy group for a compound of the formula (8)

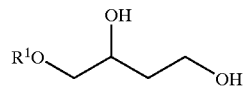
(8)

wherein $R^1$ is the same as defined above, to prepare a compound (3) and then carrying out the process of claim (2).

7. A process for preparing a compound (1) which comprises reducing a compound of the formula (9)

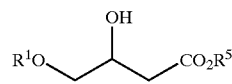
(9)

wherein $R^5$ is $C_1$–$C_6$ alkyl, $C_3$–$C_6$ cycloalkyl, phenyl, $C_1$–$C_6$ alkyl substituted phenyl, aralkyl or 2-alkenyl, and $R^1$ is the same as defined above,
  with an aluminum-reducing agent or a boron-reducing agent, to prepare a compound (8) and then carrying out the process of claim (6).

8. A process for preparing a compound (1) which comprises protecting primary hydroxy group for a compound of the formula (10)

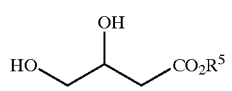
(10)

wherein $R^1$ is the same as defined above, to prepare a compound (9) and then carrying out the process of claim (7).

9. The process for preparing a compound (1) according to claim 1, comprising using compound (3) and compound (4) or (4a), wherein the protecting groups, $R^1$ and $R^2$ in compounds (3) and (4) or (4a) are different from each other and are protecting groups selected from the group of silyl ether-protecting groups, phenyl substituted methyl-protecting group and acetal-protecting groups, and that only $R^2$ is removed when the deprotection is carried out.

10. The process for preparing a compound (1) according to claim 9, wherein the protecting groups, $R^1$ and $R^2$ in compounds (3) and (4) or (4a) are a silyl ether-protecting group and a phenyl substituted methyl-protecting group, respectively.

11. The process for preparing a compound (1) according to claim 9, wherein the protective groups, $R^1$ and $R^2$ in compounds (3) and (4) or (4a) are a phenyl substituted methyl-protecting group and a silyl ether-protecting group, respectively.

12. The process for preparing a compound (1) according to claim 9, wherein the protecting groups, $R^1$ and $R^2$ in compounds (3) and (4) or (4a) are a silyl ether-protecting group and an acetal-protecting group, respectively.

13. The process for preparing a compound (1) according to claim 9, wherein the protecting groups, $R^1$ and $R^2$ in compounds (3) and (4) or (4a) are an acetal-protecting group and a silyl ether-protecting group, respectively.

14. The process for preparing a compound (1) according to claim 9, wherein the protecting groups, $R^1$ and $R^2$ in compounds (3) and (4) or (4a) are a phenyl substituted methyl-protecting group and an acetal-protecting group, respectively.

15. The process for preparing a compound (1) according to claim 9, wherein the protecting groups, $R^1$ and $R^2$ in compounds (3) and (4) or (4a) are an acetal-protecting group and a phenyl substituted methyl-protecting group, respectively.

16. The process for preparing a compound (1) according to claim 9, wherein the protecting groups, $R^1$ and $R^2$ in compounds (3) and (4) or (4a) are trityl and benzyl, respectively.

17. The process for preparing a compound (1) according to claim 2, comprising reacting compound (2), (2a) or ethylene oxide with compound (3) in an aprotic solvent.

18. The process for preparing a compound (1) of claim 17, wherein the aprotic solvent is N,N-dimethylformamide or dimethyl sulfoxide.

19. The process for preparing a compound (1) according to claim 2, comprising using an alkali metal hydride, hydroxide or carbonate as a base in reacting compound (2), (2a) or ethylene oxide with compound (3).

20. The process for preparing an optically active compound (1) according to claim 1, comprising using a optically active starting material.

21. A process for preparing a compound of the following formula (11) or its optically active compound

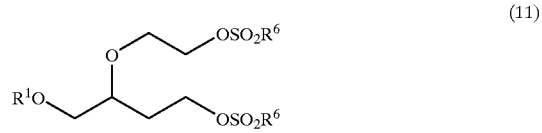

wherein $R^6$ is $C_1$–$C_6$ alkyl, $C_3$–$C_6$ cycloalkyl, phenyl, $C_1$–$C_6$ alkyl, hologen-substituted phenyl or nitro-substituted phenyl and $R^1$ is the same as defined above, which comprising preparing a compound (1) by the process of claim 1 and then subjecting the compound to sulfonyl esterification.

22. A process for preparing a compound (1) which comprises protecting a compound of the formula (7)

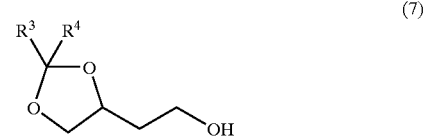

wherein $R^3$ and $R^4$ are the same or different and are hydrogen, $C_1$–$C_4$ alkyl or phenyl, or may form a $C_3$–$C_6$ cycloalkyl with the adjacent carbon atom, with a protecting agent of alcohol to prepare a compound of the formula (6)

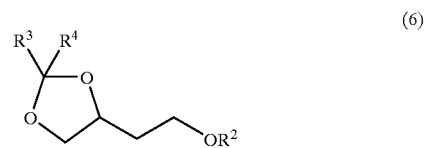

wherein $R^2$, $R^3$ and $R^4$ are the same as defined above, and then treating the compound (6) with an acid in the presence of an alcohol to prepare a compound (5) and then carrying out the process of claim (4).

* * * * *